(12) United States Patent
Chaintreau et al.

(10) Patent No.: US 7,989,013 B2
(45) Date of Patent: Aug. 2, 2011

(54) FURYL THIOALKANALS USEFUL IN THE FLAVOR INDUSTRY

(75) Inventors: Alain Chaintreau, Plan-les-Ouates (CH); Christian Starkenmann, Onex (CH); Sabine Rochat, Dardagny (CH); François Benzi, Chenex (FR)

(73) Assignee: Firmenich SA, Geneva (CH)

( * ) Notice: Subject to any disclaimer, the term of this patent is extended or adjusted under 35 U.S.C. 154(b) by 278 days.

(21) Appl. No.: 12/373,262

(22) PCT Filed: Jul. 31, 2007

(86) PCT No.: PCT/IB2007/053019
§ 371 (c)(1),
(2), (4) Date: Jan. 9, 2009

(87) PCT Pub. No.: WO2008/015638
PCT Pub. Date: Feb. 7, 2008

(65) Prior Publication Data
US 2009/0232935 A1    Sep. 17, 2009

(30) Foreign Application Priority Data

Aug. 4, 2006    (WO) .................. PCT/IB2006/052695
Aug. 25, 2006    (EP) ...................................... 06119514

(51) Int. Cl.
*A23L 2/56*    (2006.01)
*A23G 4/08*    (2006.01)
*C07D 307/34*    (2006.01)

(52) U.S. Cl. ......... 426/533; 426/534; 426/535; 549/479
(58) Field of Classification Search .................. 426/533, 426/534; 549/479
See application file for complete search history.

(56) References Cited

U.S. PATENT DOCUMENTS

| | | | |
|---|---|---|---|
| 3,697,291 A | 10/1972 | Tonsbeek | 99/107 |
| 3,930,044 A | 12/1975 | Van De Rovaart et al. | 426/533 |
| 3,930,045 A * | 12/1975 | Mosher et al. | 426/533 |
| 3,933,863 A | 1/1976 | Evers et al. | 260/347.2 |
| 3,985,907 A | 10/1976 | Evers et al. | 426/535 |
| 3,989,856 A | 11/1976 | Evers et al. | 426/535 |
| 4,031,256 A | 6/1977 | Evers et al. | 426/535 |
| 5,045,335 A * | 9/1991 | De Rooij et al. | 426/533 |
| 5,145,703 A | 9/1992 | Emberger et al. | 426/535 |

OTHER PUBLICATIONS

International Search Report PCT/IB2007/053019 Dated Jan. 31, 2008.

* cited by examiner

*Primary Examiner* — D. Lawrence Tarazano
*Assistant Examiner* — Nikki H Dees
(74) *Attorney, Agent, or Firm* — Winston & Strawn LLP

(57) ABSTRACT

The invention relates to new derivatives of 2-methyl-3-furanthiol which are useful as flavoring ingredients to confer meaty, juicy taste to a large variety of edible consumer products, chewing gums and oral care products, without imparting thereto undesirable off-notes typical of prior known furanthiol derivatives.

13 Claims, No Drawings

FURYL THIOALKANALS USEFUL IN THE FLAVOR INDUSTRY

This application is a 371 filing of International Patent Application PCT/IB2007/053019 filed Jul. 31, 2007.

TECHNICAL FIELD

The present invention relates to the flavor industry and more particularly it concerns new ingredients capable of imparting useful taste to foods and other edible consumer products. The compounds of the invention are derivatives of 2-methyl-3-furanthiol and obey the general formula

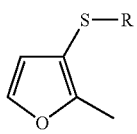

wherein R represents a group of formula

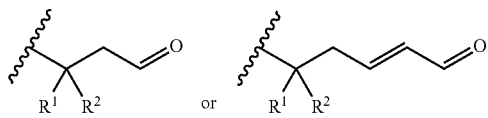

$R^1$ representing a hydrogen atom or a methyl group and $R^2$ representing a $C_1$ to $C_6$ linear or branched unsaturated hydrocarbon group.

The present invention also relates to the use of said compounds (I) to impart taste and other organoleptic properties to consumer products intended for animal or human consumption and to the compositions or end products that result from such use.

PRIOR ART

Although there are several derivatives of 2-methyl-3-furanthiol described in the prior art in relation to the flavor industry in particular, namely the alkyl sulfides described in U.S. Pat. No. 3,933,863 or yet the thioalkanones reported in U.S. Pat. No. 5,145,703, we have found no mention or suggestion of any of the compounds of formula (I) cited above. To the best of our knowledge, there is no report in the prior art of any aldehyde derivatives of the kind mentioned above, nor of their potential usefulness to create new flavoring compositions capable of modifying or improving the palatability of edible consumer products.

DESCRIPTION OF THE INVENTION

We have now surprisingly established that the compounds of formula (I) as described above possess very useful organoleptic properties and that they are capable of imparting very juicy and meaty notes to flavoring compositions and foods, beverages and other edible products. When compared to their prior known analogues, namely the thioalkanones described in U.S. Pat. No. 5,145,703, which are the closest compounds structure wise, the compounds (I) are found to bring very original connotations, and a cleaner taste than that of many other known furanthiol derivatives. The latter, when slightly overdosed, tend to bring undesired green, geranium type notes, unlike compounds (I). Given their structural similarity, this was a really surprising result.

According to a particular embodiment of the invention, there are used as flavoring ingredients the compounds of formula (I) in which R represents a group of formula

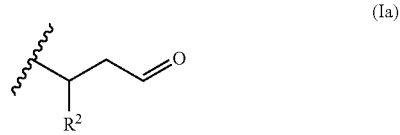

wherein $R^2$ represents a $C_1$ to $C_6$ linear or branched saturated or unsaturated hydrocarbon group.

Amongst the latter compounds (Ia), 3-[(2-methyl-3-furyl)thio]butanal is particularly appreciated for its capability to impart powerful meaty notes with a pronounced meat juice character. The flavoring properties of this ingredient are such that they make it possible to obtain an effect resembling that obtained with sulfurol, or 2-(4-methyl-1,3-thiazol-5-yl)-1-ethanol, a well-appreciated current flavoring ingredient with a nutty, cocoa type gustative character. However, the compound of the invention is far more potent taste wise and can therefore be dosed at lower concentrations to produce similar effects. In addition, we have been able to establish that this compound does not impart the undesirable musty, geranium leaves and naphthalenic notes which are typical of sulfurol and other known sulfur containing flavorants when used at higher concentrations (typically above 1 or 2 ppm, relative to the total weight of the consumer product into which they are incorporated).

In spite of the large variety of flavoring ingredients that are generally used in savory type applications in particular, to impart to foods and other edibles a meaty taste, there is always the need in the flavor industry for new ingredients capable of bringing original notes to the flavorists' palette, or yet original combinations of a variety of flavor characters, and that is exactly why 3-[(2-methyl-3-furyl)thio]butanal has turned out to be such a valued flavoring material. Because of the strength and character of its gustative note, the use of this compound is far more versatile dosage wise, compared to analogues thereof, and in particular in comparison to its structurally closest analogue, the ketone 4-[2-methyl-3-(furylthio)]-2-pentanone, as shown in the examples presented further on. When tasted in salty water (0.5% w/w of salt), at a concentration of 1 ppm, the 3-[(2-methyl-3-furyl)thio]butanal was found to impart a stronger (2 to 3 times stronger) and rounder meaty note, with a cooked and sulfurol like character, whereas 4-[2-methyl -3-(furylthio)]-2-pentanone, at the same concentration, provided a more metallic, native sulfur note.

The compounds of formula (I) are all new ingredients, each of which has its own organoleptic properties, as summarized in Table I several of these compounds.

TABLE 1

Organoleptic properties of some compounds (I)

| Compound | Dosage Ppm* | Descriptors |
|---|---|---|
| 3-[(2-methyl-3-furyl)thio]propanal | 0.1 | Oily, linoleic, juicy, common. |
| 3-[(2-methyl-3-furyl)thio]butanal | 0.1 | Meaty, juicy, powerful, nice, no off-note |
| 3-[(2-methyl-3-furyl)thio]pentanal | 0.1 | Boiled meat, beef. |
| 3-[(2-methyl-3-furyl)thio]hexanal | 0.1 | Boiled meat, beef. |
| 3-methyl-3-[(2-methyl-3-furyl)thio]butanal | 0.1 | Roasted, meat, gravy |

Favor Evaluation

TABLE 1-continued

Organoleptic properties of some compounds (I)

|  |  | Favor Evaluation |
| --- | --- | --- |
| Compound | Dosage Ppm* | Descriptors |
| 3-[(2-methyl-3-furyl)thio]nonanal | 0.1 | green; fatty; aldehydic; vegetal; seed |
| E-5-[(2-methyl-3-furyl)thio]-2-decenal | 0.1 | roasted; meat; meat juice, fatty; gravy, without off-note |

*evaluated in an aqueous salty solution (5% salt content w/w)

The compounds of the invention can be prepared using readily available raw materials, via a reaction of the so-called Michael addition type, as illustrated in Scheme I here-below.

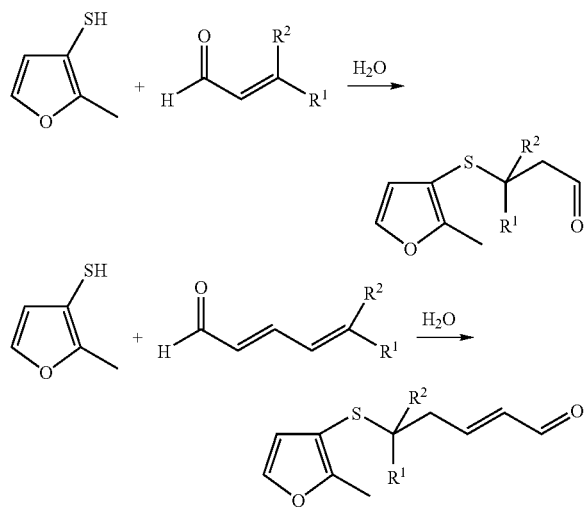

Scheme 1

These are essentially reactions between 2-methyl-3-furanthiol and an appropriate aldehyde, under conditions known to the skilled chemist and of which a more detailed description is not warranted here, specific examples being reported in the respective section of this application.

According to the invention, the precursor thiol and the appropriate aldehyde may also be generated in situ in a food or flavor composition by purposeful addition of raw materials common in Maillard type reactions. The latter involve heating a mixture of cysteine and/or or sodium hydrogen sulfide (NaHS) with an appropriate sugar composition, to generate the desired 2-methyl-3-furanthiol, to which there can be added the appropriate aldehyde in an amount sufficient to generate the desired compound (I) stoichiometrically.

Maillard type reactions may occur by simple natural food processing such as the frying, boiling, grilling or roasting of food products. The presence of amino acids and sugars in natural foods such as meat and fish leads to the formation of a variety of carbonyl, nitrogen and sulfur containing compounds upon cooking of such foods. 2-Methyl-3-furanthiol is one of the most commonly encountered sulfur precursors. Upon the cooking of such foods however, very complex mixtures of chemicals, and in particular sulfur containing derivatives are generated, and it is impossible to control the amount of each ingredient present in the mixture.

Preferably, any chemical mixture resulting directly from a chemical synthesis, e.g. without an adequate purification, in which the compound of the invention would be involved as a starting, intermediate or end-product, would not be considered as a flavoring composition according to the invention.

However, given the above comments, the invention includes a product of the chemical reactions of the Maillard type between cysteine, or another appropriate sulfur source such as hydrogenosulfide (NaHS), with an appropriate food grade sugar and a food grade aldehyde, used in amounts capable of generating the desired compound (I) in situ in a food, or separately in a form allowing addition thereof to an edible product or composition, in an amount of at least 0.01 ppm, preferably comprised between 0.01 and 2 ppm, more preferably between 0.1 and 1 ppm, and even more preferably between 0.2 and 0.5 ppm, relative to the total weight of said food or edible product.

It has in fact been now established that, under certain conditions, a reaction as described above leads to the formation of the compounds of the invention. This is an advantageous result, which could not have been anticipated from the general knowledge in the art, given that there is no mention or suggestion in the prior art of the occurrence of any of these compounds in cooked natural foods, nor generated synthetically, in spite of the large amount of studies carried out in cooked foods, such as meat and fish, which are known to contain 2-methyl-3-furanthiol.

Moreover, in addition to the fact that none of these compounds have been taught in the prior art, there is also strictly no teaching or suggestion of the possible usefulness of any of compounds (I) when added to a flavor composition prepared by admixing other common ingredients with one or more compounds (I), to create flavoring compositions capable of imparting meaty notes to a variety of edible products.

The invention thus also relates to flavors, flavoring compositions or flavored products to which the compounds (I) have been purposely added, or in which they have been purposely generated in situ by addition of the appropriate precursors, in concentrations allowing their effect to enhance the taste of the food or flavored product.

According to advantageous embodiments of the invention, the compounds (I) are prepared separately by the methods illustrated above in Scheme I, and added to the food or aromatic composition that one wants to aromatize, in amounts sufficient to impart the desired organoleptic effect.

The compounds (I) are therefore also advantageously used in a form which is devoid of the presence of any other derivative, in particular a sulfur derivative, possibly generated in a Maillard type reaction between cysteine, an appropriate sugar and an appropriate aldehyde, and/or between hydrogensulfide (NaHS), an appropriate sugar and an appropriate aldehyde.

The claim to a compound of formula (I) is however not meant to include any compound (I) naturally generated by fortuitous occurrence in a natural substance, food or ingredient, such that such natural substance, food or ingredient is hereby disclaimed.

The claimed invention includes however any composition or food product in which any compound (I) is purposely generated by such a reaction, i.e. is engendered on purpose in situ by the addition thereto of appropriate raw material precursors, under conditions allowing them to react and generate said compound (I) when the food is cooked, in an amount of at least 0.01 ppm, preferably comprised between 0.01 and 2 ppm, more preferably between 0.1 and 1 ppm, and even more preferably between 0.2 and 0.5 ppm, relative to the total weight of said food or edible product.

As mentioned above, the invention also concerns the use as flavoring ingredients of the compounds of formula (I). In other words, it concerns a method to confer, enhance, improve or modify the flavor properties and gustative character of a flavoring composition or of a flavored article, which method comprises adding to said composition or article an effective amount of at least a compound of formula (I).

By "use of a compound of formula (I)" we mean to include here the use of any composition containing compound (I) together with solvents or adjuvants of current use in the flavor industry, and which may also contain flavoring co-ingredients intended to impart other gustative characters. It is in fact current for the skilled flavorist to admix a large variety of compounds to obtain a finished composition or flavor, which can then be advantageously used to impart taste and/or texture to foods, beverages, oral care products such as toothpastes and mouthwashes, pharmaceutical products, animal feeding products and any other consumer product whose taste can be modified and/or improved by such addition of the flavoring composition, or flavor. The flavors containing compounds (I) are also an object of the present invention.

Therefore, another object of the present invention is a flavoring composition comprising:
i) as flavoring ingredient, at least one compound of formula (I) as defined above;
ii) at least one ingredient selected from the group consisting of a flavor carrier and a flavor base; and
iii) optionally at least one flavor adjuvant.

By "flavor carrier" we mean here a material which is essentially neutral from a taste point of view, i.e. that does not significantly alter the organoleptic properties of flavoring ingredients. Such carriers can be in a solid or liquid state.

As liquid carrier one may cite, as non-limiting examples, an emulsifying system, i.e. a solvent and a surfactant system, or a solvent commonly used in flavors. A detailed description of the nature and type of solvents commonly used in flavors cannot be exhaustive. However, one can cite, as non-limiting examples, solvents such as dipropyleneglycol, triacetine, diethyl phthalate, isopropyl myristate, benzyl benzoate, 2-(2-ethoxyethoxy)-1-ethanol or ethyl citrate, which are the most commonly used. As non-limiting examples of solvents commonly used in flavors, one can cite compounds such as propylene glycol, triacetine, triethyl citrate, benzylic alcohol, ethanol, vegetable oils, in particular Neobee®, or terpenes.

As a solid carrier one may cite, as non-limiting examples, absorbing gums or polymers, or yet encapsulating materials. Examples of such materials, for example, may comprise wall-forming and plasticizing materials, such as mono-, di- or tri-saccharides, natural or modified starches, hydrocolloids, cellulose derivatives, polyvinyl acetates, polyvinyl alcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualitat, Behr's Verlag GmbH & Co., Hamburg, 1996. The encapsulation is a well known process to a person skilled in the art of creating and processing flavors, and may be performed, for instance, using techniques such as spray-drying, agglomeration or yet extrusion; or it may consist of typical coating encapsulation methods, including coacervation and complex coacervation techniques.

Other carriers generally used for example in oral care edibles, are formed of edible films based on pullulan for example. Recent products of this type are very popular for breath freshening.

Generally speaking, by "flavor base or composition" we mean here a composition comprising at least one flavoring co-ingredient.

Said flavoring co-ingredient of a chosen compound (I) may be another compound of formula (I), but will more typically be a compound with a formula different from the latter and which complements, and harmonizes with, the flavoring effect provided by said chosen compound (I).

Moreover, by "flavoring co-ingredient" it is meant here a compound that is used in flavoring preparations or compositions to impart a gustative, and possibly also a texture, effect to the composition and thus modify its taste. In other words, such a co-ingredient will be recognized by a person skilled in the art as being able to impart or modify in a desired and positive or pleasant way the taste and/or texture of a composition or product, and not just as having a taste.

The nature and type of the flavoring co-ingredients present in the base does not warrant a more detailed description here, which in any case would not be exhaustive, the skilled person being able to select them on the basis of his or her general knowledge and according to the intended use or application and taste to be imparted thereto. In general terms, these flavoring co-ingredients belong to chemical classes as varied as alcohols, aldehydes, ketones, esters, ethers, acetates, nitriles, terpene hydrocarbons, nitrogenous or sulphurous heterocyclic compounds and essential oils, and said flavoring co-ingredients can be of natural or synthetic origin. Many of these co-ingredients are in any case listed in reference texts such as the book by S. Arctander, Perfume and Flavor Chemicals, 1969, Montclair, N.J., USA, or Fenaroli's Handbook of Flavor Ingredients, 1975, CRC Press; Synthetic Food Adjuncts, 1947, by M. B. Jacobs, edited by Van Nostrand, or their more recent versions, or in other works of a similar nature, as well as in the abundant patent and other literature relating to the flavor industry and to flavoring ingredients in general. It is also understood that said co-ingredients may also be materials and substances known to release in a controlled manner various types of flavoring compounds, either via chemical reactions that can be triggered by heat, pH variation or other known mechanisms, or through a physical change of said material such as dissolution, melting or other.

According to a particular embodiment of the invention, specially useful flavors and flavor bases are those capable of imparting savory and spicy notes to the edible or chewable products, in particular meat type tastes, and even more specifically beefy notes, possibly combined with "burnt, caramel, nutty and/or juicy" characters. The application examples presented further on, illustrate, without being intended to represent the full application potential of the invention's compounds and compositions, the types of gustative and texture effects which the compounds of the invention help create and their effect on the foods and other consumer products exemplified.

It is clear however that many other types of organoleptic effects can be created with the compounds (I) and the flavors and flavoring compositions containing them, the skilled flavorists and food application technologists being perfectly capable, without undue effort, of varying the ways in which they use these compounds, and the concentrations in which they are used, as a function of the consumer product to be flavored and of the particular taste modification that it is desired to achieve.

Generally speaking, by "flavor adjuvant" it is meant here an ingredient or mixture of ingredients capable of imparting additional added benefits such as a color, a particular light resistance, chemical stability, etc to the flavor in which a compound (I) is incorporated. A detailed description of the nature and type of adjuvant commonly used in flavoring bases cannot be exhaustive, but it has to be mentioned that said ingredients are well known to a person skilled in the art.

The invention also relates to compositions consisting of at least one compound of formula (I) and at least one flavor carrier, which represent particular embodiments thereof. The flavor carrier may be a liquid as mentioned above, or a solid matrix type component as is typical when the flavor is encapsulated for example, to retain its properties in an intact state until application, or to simply modify the physical properties of compound (I) or of any flavor containing it. Other current examples of flavor carriage are combinations of flavors with solid food fillers or ingredients compatible with the flavor.

It is useful to mention here that the possibility of combining in the flavors or flavoring compositions of the invention more than one compound of formula (I) is very useful as it enables the flavorist to prepare accords and flavors possessing the flavor tonality of various compounds of the invention, creating thus new tools for their flavor palette.

According to preferred embodiments of the invention, the flavoring compositions will comprise 3-[(2-methyl-3-furyl)thio]butanal in an amount sufficient to modify the taste and mouthfeel of the end product into which this compound, and/or the flavor containing it, are incorporated. This compound has been found to create an improved meat taste that resembles the taste imparted by sulfurol, with an enhanced meat juice character, and a rounded, mouthfeel enhancing effect. Moreover, this compound can be used in amounts above 2 ppm, of up to 6 ppm and more, in a finished product, without any off-note of the musty, geranium leaves and naphthalenic type, characteristic of many sulfur containing ingredients useful in meat type flavors, including sulfurol.

A compound of formula (I) can also be advantageously incorporated into products traditionally flavored to positively impart, or modify, the taste and/or texture and mouthfeel of said products. Consequently, a flavored product or article comprising:

i) as flavoring ingredient, at least one compound of formula (I), as defined above, or a flavoring composition containing this compound; and ii) a foodstuff or a chewable product base, or an oral care product base, is also an object of the present invention.

For the sake of clarity, it has to be mentioned that, by a "foodstuff or a chewable product base", we mean here the base composition of an edible product, e.g. a food or a beverage or other edible product, or of a chewable article such as a chewing gum or a tablet, namely a pharmaceutical tablet. This refers to the basic composition or formulation of the edible or chewable product, without the flavor compounds or compositions, such that the claimed invention is the combination of said base with the compound or compounds (I), or with the flavoring compositions containing them. As oral care basic formulations we mean to include here toothpastes and breath freshening preparations in the form of edible films, as well as mouthwashes.

The nature and type of the constituents of the foodstuffs, beverages and other edible or chewable consumer products, do not warrant a more detailed description here, which in any case would not be exhaustive, the skilled person being able to select them on the basis of its general knowledge and according to the nature of said product.

The compounds (I) and the flavors containing them can be incorporated in any type of product traditionally flavored to modify its taste and/or texture. Non-limiting examples of suitable foodstuff and chewable bases include bakery and confectionery products, chewing gums and breath freshening films, meat, vegetable or fish stock cubes for the preparation of soups, sauces or gravies, ready to cook or ready to eat foods such as soups, gravies, sauces, pizzas, meat preparations, cheese preparations, marinades and coatings for meat and fish, preparations to be injected into meat or fish, chips and savory crackers, vegetable preparations, etc. In particular, the preferred compound of the invention, 3-[(2-methyl-3-furyl)thio]butanal, has been found to be very useful in all these types of consumer products, as well as in dairy type applications such as milk, cooked milk, caramel, custard, sabaillon and yoghurt type applications. Its flavoring effect in confectioneries such as hard-boiled candies is also much appreciated.

The proportions in which the compounds according to the invention can be incorporated into the various aforementioned articles or products vary within a wide range of values. These values are dependent on the nature of the article to be flavored and on the desired organoleptic effect, as well as the nature of the co-ingredients in a given base, when the compounds according to the invention are mixed with flavoring co-ingredients, solvents or additives commonly used in the art.

In the case of flavoring compositions or flavors, i.e. mixtures of ingredients capable of imparting taste and together with common solid or liquid carriers, such as solvents, typical concentrations of compounds (I) are in the order of 0.001% to 5% by weight, or even more, of the compounds of the invention, based on the weight of the flavoring composition. Concentrations lower than these, such as in the order of 0.01% to 0.5% by weight, can be used when these compounds are incorporated into flavored products, percentage being relative to the weight of the product. Thus typical concentrations of compounds (I), and in particular of preferred 3-[(2-methyl-3-furyl)thio]butanal will be in an amount of at least 0.01 ppm, preferably comprised between 0.01 and 2 ppm, more preferably between 0.1 and 1 ppm, and even more preferably between 0.2 and 0.5 ppm, relative to the total weight of said food or edible product.

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 400 MHz machine for $^1H$ and $^{13}C$, the chemical displacements δ are indicated in ppm with respect to TMS as standard, the coupling constants J are expressed in Hz.

Examples 1-8

Synthesis of Compounds of Formula (I) by Using the Appropriate Raw Materials in the Reactions Represented in Scheme (I)

A. Synthesis of 3-[(2-methyl-3-furyl)thio]alkanals and 3-methyl -3-[(2-methyl-3-furyl)thio]alkanals As a typical synthesis, 2-methyl-3-furanethiol (hereinafter designated as MFT), a 2-alkenal, distilled water and ethanol were stirred at room temperature for several hours (24-95 h) according to the proportions reported in Table II. Then the reaction mixture was extracted with diethyl ether (2 times) and the organic layers washed with a saturated solution of NaCl. The combined organic layer was dried over $Na_2SO_4$ and concentrated. The pure compound was obtained after column chromatography ($SiO_2$, heptane/diethyl ether 8:2)

TABLE II

Preparation conditions of 3-methyl-3-[(2-methyl-3-furyl)thio]alkanals.

| Aldehyde/Conc. mMol | MFT mMol | Water ml | EtOH ml | Stirring time/h | Purification | Yield % |
|---|---|---|---|---|---|---|
| E-2-propenal/26.31 | 26.31 | 15.0 | 9.0 | 24 | SiO$_2$ | 50.8 |
| E-2-butenal/26.31 | 26.31 | 15.0 | 9.0 | 24 | SiO$_2$ | 40.1 |
| E-2-pentenal/22.00 | 22.00 | 12.5 | 7.5 | 24 | SiO$_2$ | 61.1 |
| E-2-hexenal/29.10 | 26.31 | 15.0 | 9.0 | 48 | SiO$_2$ | 53.6 |
| E-2-nonenal/31.52 | 26.27 | 15.0 | — | 95 | Distillation | 46.7 |
| E-3-methyl-2-butenal/39.50 | 26.31 | 15.0 | 9.0 | 48 | SiO$_2$ | 42.8 |

B. Synthesis of (2E)-5-[(2-methyl-3-furyl)thio)-2-alkenals

2-Methyl-3-furanethiol (MTF), the (E,E)-2,4-alkadienal and distilled water were stirred at ambient temperature for several hours under the conditions reported in Table III. The resulting compound was first purified by column chromatography (SiO$_2$, toluene/ethyl acetate 9:1) to give a mixture of (+-)-(2E)-5-[(2-methyl-3-furyl)thio)-2-alkenal and (E,E)-2,4-alkadienal. Bulb to bulb distillation delivered the (E,E)-2,4-R-dienal and allowed recovery of the (2E)-5-[(2-methyl-3-furyl)thio)-2-alkenal in the residues. A second column chromatography (SiO$_2$, toluene/ethyl acetate 9:1) yielded the desired pure product.

TABLE III

Preparation conditions of (2E)-5-[(2-methyl-3-furyl)thio)-2-alkenals

| Aldehyde/Conc. mMol | MFT mMol | Water ml | EtOH ml | Stirring time/h | Purification | Yield % |
|---|---|---|---|---|---|---|
| E-E-2,4-nonadienal/23.90 | 26.27 | 15 | No | 24 | Dist. + SiO$_2$ | |
| E-E-2,4-decadienal/17.36 | 17.54 | 10 | No | 63 | Dist. + SiO$_2$ | 36.64 |

C. Analytical Data

I. 3-[(2-methyl-3-furyl)thio]propanal $^{13}$C NMR 200.53 (d); 155.55 (s); 140.89 (d); 114.91 (d); 109.14 (s); 43.62 (t); 28.28 (t); 11.77 (q).
$^{1}$H NMR 9.74-9.71 (t, J=1.28, 1H); 7.29 (d, J=2.1, 1H); 6.34 (d, J=2.1, 1H); 2.93-2.86 (t, J=7.2, 2H); 2.69-2.63 (t, J=6.9, 2H); 2.33 (s, 3H).
MS M$^{+\cdot}$=170 (68); m/e: 114 (100); 86 (26); 81 (8); 71 (15); 69 (12); 59 (10); 53 (8); 51 (15); 45 (17); 43 (23); 39 (5); 29 (8); 27 (10).

II. 3-[(2-methyl-3-furyl)thio]butanal $^{13}$C NMR 200.56 (4); 156.69 (s); 140.74 (4); 115.98 (4); 107.79 (s); 50.18 (t); 37.99 (d); 14.12 (q); 11.90 (q).
$^{1}$H NMR 9.74-9.72 (t, J=1.8, 1H); 7.30 (d, J=2.1, 1H); 6.33 (d, J=2.1, 1H); 3.43-3.33 (s, J=7.0, 1H); 2.68-2.46 (m, 2H); 2.34 (s, 3H); 1.30 (d, J=6.7, 3H).
MS M$^{+\cdot}$=184 (60); m/e: 114 (100); 86 (38), 81 (12); 71 (18); 69 (12); 59 (9); 53 (8); 51 (12); 45 (13); 43 (30); 41 (19); 39 (15); 29 (6); 27 (9).

III. 3-[(2-methyl-3-furyl)thio]pentanal $^{13}$C NMR 200.92 (d); 156.66 (s); 140.75 (d); 115.93 (d); 107.57 (s); 48.16 (t); 45.07 (d); 27.59 (t); 11.93 (q); 11.49 (q).
$^{1}$H NMR 9.75-9.73 (t, J=2.0, 1H); 7.29 (d, J=2.0, 1H); 6.32 (d, J=1.5, 1H); 3.20-3.11 (m, 1H); 2.59-2.54 (m, 2H); 2.33 (s, 3H); 1.64-1.55 (m, 2H); 1.09-1.03 (t, J=7.4, 3H).
MS M$^{+\cdot}$=198 (39); m/e: 114 (100); 86 (30); 71 (16); 59 (9); 57 (11); 55 (20); 51 (8); 45 (16); 43 (30); 41 (27); 39 (15); 29 (15); 27 (27).

IV. 3-[(2-methyl-3-furyl)thio]hexanal $^{13}$C NMR 200.95 (d); 156.69 (s); 140.76 (d); 115.97 (d); 107.51 (s); 48.61 (t); 43.15 (d); 36.76 (t); 20.17 (t); 13.77 (q); 11.91 (q).
$^{1}$H NMR 9.75-9.72 (t, J=2.0, 1H); 7.29 (d, J=2.0, 1H); 6.31 (d, J=1.5, 1H); 3.27-3.18 (m, 1H); 2.59-2.54 (m, 2H); 2.32 (s, 3H); 1.61-1.42 (m, 4H); 0.96-0.90 (t, J=7.2, 3H).
MS M$^{+\cdot}$=212 (31); m/e: 114 (100); 86 (23); 81 (22); 71 (15); 69 (20); 59 (8); 57 (13); 55 (39); 53 (13); 51 (15); 45 (13); 43 (38); 41 (31); 39 (21); 29 (17); 27 (16).

V. 3-methyl-3-[(2-methyl-3-furyl)thio]butanal $^{13}$C NMR 201.75 (4); 157.99 (s); 140.62 (4); 116.86 (4); 107.37 (s); 54.22 (t); 46.56 (s); 28.79 (q); 12.11 (q).
$^{1}$H NMR 9.91-9.88 (t, J=2.8, 1H); 7.32 (d, J=2.1, 1H); 6.33 (d, J=2.1, 1H); 2.48 (d, J=3.1, 2H); 2.35 (s, 3H); 1.40 (s, 6H).
MS M$^{+\cdot}$=198 (20); m/e: 114 (100); 86 (18); 71 (7); 57 (10); 45 (5); 43 (10); 41 (17); 39 (6); 29 (9).

VI. (2E)-5-[(2-methyl-3-furyl)thio)-2-decenal $^{13}$C NMR 193.68 (d); 156.17 (s); 155.31 (d); 140.76 (d); 134.56 (d); 115.70 (d); 108.26 (s); 48.32 (d); 37.72 (t); 34.16 (t); 31.61 (t); 26.63 (t); 22.56 (t); 14.02 (q); 11.99 (q).
$^{1}$H NMR 9.54 (d, J=8.19, 1H); 7.30 (d, J=2.04, 1H); 6.95-6.87 (m, 1H); 6.30 (d, J=1.54, 1H); 6.16 (q, J=7.85, 1H); 2.87 (t, J=6.15, 1H); 2.53 (t, J=6.91, 2H); 2.33 (s, 3H); 1.35-1.20 (m, 8H); 0.90 (t, J=6.91, 3H).
MS M$^{+\cdot}$=226 (17); m/e: 197 (12); 153 (15); 140 (7); 127 (9); 114 (97); 95 (11); 81 (100); 67 (25); 55 (31); 43 (27); 41 (41); 29 (18).

VII. 3-[(2-methyl-3-furyl)thio]nonanal $^{13}$C NMR 200.95 (d); 156.65 (s); 140.82 (d); 115.95 (d); 107.57 (s); 48.62 (t); 43.43 (d); 34.67 (t); 31.71 (t); 29.02 (t); 26.94 (t); 22.60 (t); 14.06 (q); 11.92 (q).
$^{1}$H NMR 9.73 (s, 1H); 7.31-7.26 (m, 1H); 6.39-6.30 (m, 1H); 3.25-3.17 (m, 1H); 2.56 (d, J=6.66, 2H); 2.32 (s, 3H); 1.53 (t, J=4.61, 3H); 1.29 (s, 7H); 0.89 (t, J=0.89, 3H)

MS M$^+$=254 (24); m/e: 114 (100); 96 (8); 85 (13); 83 (18); 81 (20); 70 (21); 57 (140); 55 (30); 43 (29); 41 (25); 29 (11).

Example 9

Synthesis of 3-[(2-methyl-3-furyl)thio]butanal via Maillard Reaction Intermediates A. Reaction of Cysteine with Xylose Followed by the Addition of Natural Crotonaldehyde A large excess of cysteine (2.4 g, 20 mmole) was reacted with xylose (0.3 g, 2 mmole) and NaH2PO4 (2 g, 100 mmole). The components were dry blended with hydromatrix (amorphous carrier; Varian part 198003) (17 g). In an ASE (Accelerated Solvent Extraction) cell from Dionex, water was added (60-70 ml) and the mixture was heated at 150° C. The pressure was adjusted to 100 bars with nitrogen during one static cycle of 30 min. Natural crotonaldehyde (1.4 g, 20 mmole) was added to the crude process flavor product released from the cell (pH 6.5). Before the addition of crotonaldehyde, an aliquot representing 10% of the reaction mixture was extracted with pentane containing 1 mg/ml of octanethiol as an internal standard, and analyzed by GC-MS. After the addition of crotonaldehyde, the same extraction was performed. The presence of 3-[(2-methyl -3-furyl)thio]butanal was confirmed at the expected retention time in the second case, whereas no presence of the product was detected in the absence of crotonaldehyde.

B. Reaction of Sodium Hydrogenosulfide with Xylose, Followed by the Addition of Natural Crotonaldehyde NaHS (Acros 70%) (128 mg, 2 mmole), xylose (0.3 g, 2 mmole), NaH$_2$PO$_4$ (2 g, 100 mmole) were dry blended with hydromatrix (Varian part 198003) (17 g). In an ASE cell, water was added (60-70 ml) and heated at 150° C. The pressure was adjusted at 100 bars with nitrogen during one static cycle of 30 min. The reaction mixture was extracted with pentane containing 1 mg/ml of octanethiol as an internal standard and analyzed by GC-MS.

Natural crotonaldehyde (140 mg, 2 mmole) was added to the crude process flavor released from the cell (pH 6.5). The reaction mixture was extracted with pentane (50 ml), dried on Na$_2$SO$_4$ and concentrated. The residue was re-diluted to 2 ml in a volumetric flask and analyzed by GC-MS. The presence of 3-[(2-methyl-3-furyl)thio]butanal was confirmed (spectrum and retention time). The chemical yield calculated from NaHS was estimated at 0.01%.

C. One Pot, One-Step Reaction of Hydrogenosulfide, Xylose, Glucose and Alanine

A mixture of NaHS (17.6 g, 220 mmole), xylose (22.5 g, 150 mmole), glucose (27 g, 150 mmole) and alanine (26.7 g, 300 mmole) in water (1 g), buffered with NaH$_2$PO$_4$ (60 g, 200 mmole), was heated in an autoclave at 80-100° C. for one hour. The water was first added, followed by NaH$_2$PO$_4$, then the xylose, glucose, alanine and NaHS. The autoclave was immediately sealed after addition of the reagents to ensure that there was no loss of volatile products formed such as H$_2$S and acetaldehyde. After cooling down and extraction with diethylether, the presence of 3-[(2-methyl-3-furyl)thio]butanal was confirmed in the reaction mixture by GC/MS analysis in SIM mode which gave a GC peak at the expected retention time of 21.9 min, via identification of the MS fragments m/z 86, 114 and 184.

Comparative Example

Synthesis of 4-[(2-methyl-3-(furylthio)]pentanone

According to U.S. Pat. No. 5,145,703, 5 g of 2-methyl-3-furanthiol (43.85 mmol) and 7.5 g of 3-penten-2-one (89.28 mmol) were dissolved in 50 ml of ethanol. The solution was stirred for 60 hours at room temperature. The solvent was then distilled off in vacuum at 50° C. The residue, 10.38 g, was purified by column chromatography (SiO$_2$, toluene/ethyl acetate 8:2) and afforded 4.41 g (18%) of a yellow oil (46.70%).

$^{13}$C NMR 206.45 (s); 156.35 (s); 140.57 (d); 116.02 (d); 108.33 (s); 50.49 (t); 38.82 (d); 30.42 (q); 21.06 (q); 11.88 (q).

$^1$H NMR 7.29 (d, J=1.54, 1H); 6.33 (d, J=2.05, 1H); 3.39-3.28 (m, 1H); 2.74-2.65 (m, 1H); 2.54-2.45 (m, 1H); 2.34 (s, 3H); 2.13 (s, 3H); 1.23 (t, J=6.66, 3H).

MS M$^+$=198 (36); m/e: 114 (100); 85 (22); 71 (13); 69 (62); 59 (6); 53 (10); 51 (10); 45 (11); 43 (78); 41 (31); 39 (19).

Gustative note: the compound was evaluated in a saline solution (5% salt, w/w) and compared to its aldehyde homologue on a blind test; both compounds were used at 1 ppm in the saline solution; present compound was found to have a more metallic character, more raw sulfur, than the 3-[(2-methyl-3-furyl)thio]butanal of the invention, and a flavor strength about 2 to 3 times inferior.

Example 10

Use of 3-[(2-methyl-3-furyl)thio]butanal as a Flavouring Ingredient in Savory Type Flavors and Applications Thereof The above-mentioned compound was added to a variety of flavor compositions (origin: Firmenich S A, Geneva, Switzerland) having savory connotations of the type indicated in Table IV, in the amounts indicated. The positive organoleptic effect observed in all cases as a result of blind test evaluations, as compared to the known flavors without the compound of the invention, is summarized in the table. The evaluation tests were carried out on blind tests, using aqueous solutions comprising the ingredients indicated, in the proportions listed (MSG stands for monosodium glutamate).

TABLE IV

Performance of 3-[(2-methyl-3-furyl)thio]butanal in a variety of savory type flavors (the increasing number of stars indicates an increased level of flavour improvement).

| Flavor connotation type | Flavor code | Flavor dosage* (%) | Title compound dosage* (ppm) | Application Formula solution | Evaluation & rating |
|---|---|---|---|---|---|
| Smoke | 502013 T | 0.002 | 0.01-1.0 | Salt 0.5% MSG 0.05% | Covers the harsh phenolic notes, at higher level imparts a strong bacon character.*** |

TABLE IV-continued

Performance of 3-[(2-methyl-3-furyl)thio]butanal in a variety of savory type flavors (the increasing number of stars indicates an increased level of flavour improvement).

| Flavor connotation type | Flavor code | Flavor dosage* (%) | Title compound dosage* (ppm) | Application Formula solution | Evaluation & rating |
|---|---|---|---|---|---|
| Mortadella | 503733 TH | 0.002 | 0.01–1.0 | Salt 0.5% MSG 0.05% | Rounds off the spices and increases meatiness according to the level. No off notes.*** |
| Cooked ham | 053072 A | 0.008 | 0.01–0.05 | Salt 0.5% MSG 0.05% | Increases meatiness, rounds off the whole, imparts lastingness in the mouth.*** |
| Lamb | 569261 TH | 0.001 | 0.005–0.03 | Salt 0.5% MSG 0.05% | Increases the mutton character (might need to be decreased), but overall rounder.** |
| Hydrolyzed vegetable protein replacer | 569251 T | 0.003 | 0.02–0.5 | Salt 0.5% MSG 0.05% | Rounds off, brings authenticity, at high levels impart a fermented, yeasty, soya sauce character.*** |
| Beef | 505443 AH | 0.008 | 0.02–0.1 | Salt 0.5% MSG 0.05% | More juicy, meaty, sweet, slightly onion juice like.*** |
| Chicken | 569334 TH | 0.0015 | 0.005–0.02 | Salt 0.5% MSG 0.05% | Increases the feathery notes (thiol, dimethylthiol) and imparts a dark meat character.** |
| Chicken broth | 569619 TH | 0.004 | 0.02–0.2 | Salt 0.5% MSG 0.05% | Increases the nutty, buttery notes, turns the flavor into turkey profile.** |
| Boiled Chicken | 569730 TH | 0.002 | 0.01–0.05 | Salt 0.5% MSG 0.05% | Pushes unsaturated aldehydes, imparts a darker, turkey-like character.*** |
| Mushroom button | 569221 TH | 0.002 | 0.03–0.5 | Salt 0.5% MSG 0.05% | Rounder, fuller, brings mouthfeel and authenticity.*** |
| Onion fried ring | 700310 03NF | 0.003 | 0.02–0.2 | Salt 0.5% MSG 0.05% | Rounds off, brings authenticity and depth. Increases lastingness*** |
| Cheese | 504897 T | 0.004 | 0.02–0.4 | Salt 0.5% MSG 0.05% | Increases process cheese character, from mature type to melted cheese.*** |
| Vegetable soup | 505822 TH | 0.003 | 0.02–0.3 | Salt 0.5% MSG 0.05% | Gives well defined vegetable notes, such as carrot, celery, cauliflower. Effect. at high level, increases salivation.*** |
| Pizza | 569163 TH | 0.003 | 0.03–0.3 | Salt 0.5% MSG 0.05% | At lower level, the whole pizza character performs better, rounds off the whole.*** |

*in application, relative to the total weight of flavored consumer product.

Example 11

Use of 3-[(2-methyl-3-furyl)thio]butanal as a Flavouring Ingredient in Specific Flavor Compositions a) Tomato Type Flavor A typical flavor having a tomato character was prepared by admixing the following ingredients in the amounts indicated:

| Ingredients | Parts by weight |
| --- | --- |
| Octanoic acid | 10.000 |
| Aldehyde C6 | 20.000 |
| Propanal | 5.000 |
| Damascenone at 50.00%* | 5.000 |
| Ethylpyridine | 5.000 |
| 5-Decanolide at 10.00%* | 30.000 |
| Guaiacol at 10.00%* | 15.000 |
| Hydroxyacetophenone at 1.00%* | 30.000 |
| Methylthiofurane at 1.00%* | 60.000 |
| Diallyl disulfide at 1.00%* | 5.000 |
| Ortho-cresol at 1.00%* | 20.000 |
| Transpentenal | 15.000 |
| Triacetine | 305.000 |
| Vanilline at 10.00%* | 10.000 |
| Isobutyl acetate | 30.000 |
| Linalyl caproate | 30.000 |
| Eugenol | 5.000 |
| Methylfurfural | 60.000 |
| Methylheptenone | 60.000 |
| Methylmercaptan at 1.00%** | 30.000 |
| 3-(Methylthio)propanal | 70.000 |
| Dimethyl sulfide | 150.000 |
| Terpineol ord | 30.000 |
| Total | 1000.000 |

*In triacetine
**In ethyl citrate

To this flavor there was added 3-[(2-methyl-3-furyl)thio]butanal in an amount sufficient to provide a final concentration of 0.01 to 0.1 ppm of this compound in a tasting saline solution (salt 0.5%, MSG 0.05% w/w) where the tomato flavor was used in an amount of 0.010 ppm. A blind test evaluation showed that the compound of the invention provided a rounding effect to the flavor and added some mouthfeel to the flavor composition.

b) Bacon Type Flavor

A typical flavor having a bacon character was prepared by admixing the following ingredients in the amounts indicated:

| Ingredients | Parts by weight |
| --- | --- |
| Acetylpyrazine at 1.00%* | 25.000 |
| Carvacrol redist | 5.000 |
| Benzylsulfide at 10.00%* | 5.000 |
| 2,4-Nonadienal at 1.00%* | 15.000 |
| Dimethylbenzofurane at 10.00%* | 15.000 |
| 2-Ethyl-3-methyl pyrazine at 10.00%* | 35.000 |
| 4,5-Dihydro-2-methyl-3(2H)-thiophenone at 10.00%* | 25.000 |
| 5-Ethyl-3-hydroxy-4-methyl-2(5H)-furanone at 1.00%* | 20.000 |
| Octenal at 10.00%* | 10.000 |
| Ortho-cresol at 10.00%* | 5.000 |
| Quinoleine at 10.00%* | 25.000 |
| Vanilline at 10.00%** | 35.000 |
| Acetylpropionyle | 25.000 |
| Acetic acid | 60.000 |
| Nonanoic acid | 60.000 |
| Methylnussol at 1.00%*** | 15.000 |
| Decanoic acid | 60.000 |
| Isobutyric acid | 35.000 |
| Char oil | 250.000 |
| 5-Dodecanolide | 15.000 |
| Furaneol ®[1] | 30.000 |
| Guaiacol | 35.000 |
| Isoeugenol extra | 60.000 |
| 6-Methyl-3,5-heptadien-2-one | 30.000 |
| Isopropylphenol | 25.000 |
| Labdanum essential oil at 10.00%* | 20.000 |
| 4-Ethyl-2-methoxy phenol | 20.000 |
| Nussol extra | 10.000 |
| Pyridine | 15.000 |
| 2-Methyl-1-benzenethiol | 15.000 |
| Total | 1000.000 |

*In Neobee ®
**In triacetine
***In ethyl citrate
[1]Origin: Firmenich SA, Geneva, Switzerland To this flavor composition there was added 3-[(2-methyl-3-furyl)thio]butanal in an amount sufficient to provide a final concentration of 0.02 to 1 ppm of this compound in a tasting saline solution (salt 0.5%, MSG 0.05% w/w) where the bacon flavor was used in an amount of 0.003 ppm. A blind test evaluation of the flavor showed that the compound of the invention was found to enhance the moss, walnut, maple character of the flavor and was very suitable for use with brown type notes.

c) Grilled Beef Type Flavor

A typical flavor having a grilled beef character was prepared by admixing the following ingredients in the amounts indicated:

| Ingredients | Parts by weight |
| --- | --- |
| Acetylthiazole at 10.00%* | 10.000 |
| Oleic acid | 200.000 |
| Phenylacetic acid at 1.00%* | 50.000 |
| Hexanal at 0.10%* | 25.000 |
| Nonanal at 1.00%* | 50.000 |
| 3-Methyl-butanal at 1.00%* | 15.000 |
| Cafeol at 1.00%* | 60.000 |
| E,E-2,4 heptadienal at 0.10%* | 5.000 |
| 2,4-Octadienal at 0.10%* | 5.000 |
| Guaiacol at 1.00%* | 5.000 |
| Indol at 1.00%* | 50.000 |
| Ethyl dimethylpyrazine at 1.00%* | 40.000 |
| Methylfuryl disulfide at 10.00%* | 10.000 |
| Pentyl vinyl ketone at 0.10%* | 10.000 |
| Propylmercaptan at 1.00%* | 5.000 |
| Butyric acid | 25.000 |
| Beef gril renf nat triac[1] | 300.000 |
| Char oil | 15.000 |
| Furaneol ®[1] | 5.000 |
| Lauric acid | 25.000 |
| 2,3,5-Trimethylpyrazine at 10.00%* | 60.000 |
| 3-(Methylthio)propanal | 10.000 |
| Mercaptomethylbutanol at 10.00%* | 10.000 |
| Trimethylamine | 5.000 |
| Total | 995.000 |

*In oleic acid
[1]Origin: Firmenich SA, Geneva, Switzerland

To this flavor composition there was added 3-[(2-methyl-3-furyl)thio]butanal in an amount sufficient to provide a final concentration of 0.01 to 0.05 ppm of this compound in a tasting saline solution (salt 0.5%, MSG 0.05% w/w) where the flavor was used in an amount of 0.005 ppm. A blind test evaluation of the flavor showed that the compound of the invention was found to round off the whole character of the flavor and increase the hamburger character.

d) Shrimp Type Flavor

A typical flavor having a shrimp flavor character was prepared by admixing the following ingredients in the amounts indicated:

| Ingredients | Parts by weight |
|---|---|
| Acetodine | 5.000 |
| Alcohol furfurylic redist | 120.000 |
| Benzothiazole at 1.00%* | 15.000 |
| 2,6-Nonadienol at 0.10%* | 10.000 |
| 3-Octen-1-ol at 10.00%* | 20.000 |
| Dimethylphenol | 25.000 |
| Polyglycol | 60.000 |
| Ethyl hexanol K at 10.00%* | 30.000 |
| Furfural nat | 10.000 |
| E-6-methyl-3,5-heptadien-2-one | 5.000 |
| 2,3-Diethylpyrazine at 1.00%* | 5.000 |
| Methylheptenone at 10.00%* | 40.000 |
| Methylthiobutyraldehyde at 10.00%** | 20.000 |
| 3-(Methylthio)-propanal | 10.000 |
| Marin resinoine rob at 20.00%*** | 15.000 |
| (Z)-2-nonen-1-ol at 1.00%* | 10.000 |
| Dimethylsulfide | 20.000 |
| Triacetine | 440.000 |
| Trimethylamine 40 AQ | 100.000 |
| Nonanal at 0.10%* | 20.000 |
| 2,4-Nonadienal at 0.10%* | 15.000 |
| Heptenal at 0.10%* | 5.000 |
| Total | 1000.000 |

*In triacetine
**In ethyl citrate
***In polyglycol
[1]Origin: Firmenich SA, Geneva, Switzerland To this flavor composition there was added 3-[(2-methyl-3-furyl)thio]butanal in an amount sufficient to provide a final concentration of 0.1 to 1.0 ppm of this compound in a tasting saline solution (salt 0.5%, MSG 0.05% w/w) where the flavor was used in an amount of 0.008 ppm. A blind test evaluation of the flavor showed that the compound of the invention was found to render the flavor more natural-like and increase its meatiness. The compound combine very well with seafood type notes.

e) Garlic Roast Type Flavor

A typical flavor having a garlic roast type flavor character was prepared by admixing the following ingredients in the amounts indicated:

| Ingredients | Parts by weight |
|---|---|
| Acetylpyrazine at 1.00%* | 30.000 |
| Ethyl acrylate at 10.00%* | 10.000 |
| Heptanal at 10.00%* | 15.000 |
| Benzylmercaptan at 10.00%* | 15.000 |
| Caryophyllene at 10.00%* | 10.000 |
| Cis-3-hexenol formate at 1.00%* | 20.000 |
| 2,3,5-Trimethylpyrazine at 10.00%* | 70.000 |
| 2-Ethyl-3-methylpyrazine at 10.00%* | 60.000 |
| Thiol at 10.00%* | 40.000 |
| Decanoic acid redist. | 5.000 |
| Garlic essential oil | 20.000 |
| Isovalerianic aldehyde | 5.000 |
| 3-Propylidene-1-benzo(C)furanone | 10.000 |
| Benzothiazole | 20.000 |
| Furaneol ®[1] | 25.000 |
| Methylfurfural | 40.000 |
| Methylnussol at 10.00%** | 10.000 |
| Mustard essential oil | 30.000 |
| (E)-2-hexenal | 5.000 |
| Diallyl sulfide | 350.000 |
| Dipropyl disulfide | 50.000 |
| 5-Ethyl-3-hydroxy-4-methyl-2(5H)-furanone at 1.00%* | 5.000 |
| Nussol extra | 10.000 |
| Propylmercaptan at 10.00%* | 100.000 |
| Sulfurobase[1] | 30.000 |
| Dimethyl trisulfide at 10.00%* | 15.000 |
| Total | 1000.000 |

*In triacetine
**In ethyl citrate
[1]Origin: Firmenich SA, Geneva, Switzerland

To this flavor composition there was added 3-[(2-methyl-3-furyl)thio]butanal in an amount sufficient to provide a final concentration of 0.002 to 0.1 ppm of this compound in a tasting saline solution (salt 0.5%, MSG 0.05% w/w) where the flavor was used in an amount of 0.001 ppm. A blind test evaluation of the flavor showed that the compound of the invention was found to increase the roast-golden-caramelic character of the flavor and impart juiciness and salivation.

f) Sour Milk Type Flavor Composition

A typical flavor having a sour milk type flavor character, particularly useful for yoghurt type applications, was prepared by admixing the following ingredients in the amounts indicated:

| Ingredients | Parts by weight |
|---|---|
| Ethyl acetate at 10.00%* | 40 |
| Acetic acid | 50 |
| Lactic acid | 300 |
| Tartric acid | 35 |
| Ethanol | 220 |
| Furfuryl alcohol | 15 |
| Nonalactone gamma | 1 |
| Lemon oil at 10.00%* | 60 |
| Maltol | 20 |
| Diacetyl | 6 |
| Dodecalactone gamma | 1 |
| Ethyl lactate | 20 |
| Furaneol ®[1] at 15.00%* | 65 |
| Indol at 0.1%** | 45 |
| Vanilline | 20 |
| Propylene glycol | 72 |
| Total | 970 |

*In ethanol
**In triacetine
[1]Origin: Firmenich SA, Geneva, Switzerland

To this flavor composition there was added 3-[(2-methyl-3-furyl)thio]butanal (solution at 0.1% by weight in ethanol) in an amount of 30 parts by weight. In parallel, a known composition was prepared with the same flavor composition above, using 30 parts by weight of sulfurol (solution at 10% by weight in ethanol).

The two compositions thus prepared were tasted on a blind triangle test by a panel of six trained flavorists. The end product dosages in these compounds used corresponded to 0.003 ppm for the compound of the invention and 0.3 ppm for sulfurol, so as to provide comparable effects. The result of this evaluation showed that the composition containing the compound of the invention was distinctly preferred by the panel and judged to possess an improved creamy character, more condensed milk, almost animal at such a dosage. From the dosages used, it can be estimated that the impact of the 3-[(2-methyl-3-furyl)thio]butanal is around 100 times greater than that of sulfurol.

Example 12

Use of 3-[(2-methyl-3-furyl)thio]butanal as a Flavouring Ingredient in Flavored Edible Consumer Products The above-mentioned compound was added to a variety of consumer products available on the market, as described below. In some cases, similar products were prepared by adding instead prior known 4-[(2-methyl-3-(furylthio)]pentanone, described in the comparative example above. Blind evaluation tests were carried out with the various types of products and the results of the evaluations are presented below. The conditions under which the flavoring compounds were used, and their proportions, are indicated below.

A. Chicken Bouillon Cube

Tasted in a boiling solution comprising 10 g of a standard chicken bouillon base in 500 ml of water, using the following flavoring conditions:
1) without flavor
2) with a chicken type flavor (Chicken 589133 spm, origin: Firmenich S A) at 0.2% rtc (ready to consume, i.e. weight percentage in end product)
3) with a chicken type flavor (Chicken 589133 spm, origin: Firmenich S A) at 0.2% rtc plus 3-[(2-methyl-3-furyl)thio]butanal at 0.2 ppm rtc
4) with a chicken type flavor (Chicken 589133 spm, origin: Firmenich S A) at 0.2% rtc plus prior known 4-[(2-methyl-3-(furylthio)]pentanone at 0.2 ppm rtc.

Results of the evaluation (the numbers correspond to the flavoring compositions 3 and 4 indicated above, when compared, on blind tests, to the unflavored and flavored products obtained with compositions 1 and 2, and to each other):
Odor:
3) Meatier, cooked, sulfurol character
4) Less performant, less impact.
Taste:
3) Rounder, mellower/velvety, strong. Same positive effect even at 0.1 ppm dosage.
4) Weaker, different character, distinctly less mouthfeel, similar to known furanthiols.

B. Gravy Beef Sauce

Prepared a cold solution comprising 23.5 g of a standard brown gravy mix base in 500 ml of water. Mixture was brought to boiling point and cooked for 5 minutes. Products were tasted using the following flavoring conditions:
1) without flavor
2) with a beef type flavor (Beef 589051 spm, origin: Firmenich S A) at 0.2% rtc
3) with a beef type flavor (Beef 589051 spm, origin: Firmenich S A) at 0.2% rtc plus 3-[(2-methyl-3-furyl)thio]butanal at 0.3 ppm rtc
4) with a beef type flavor (Beef 589051 spm, origin: Firmenich S A) at 0.2% rtc plus prior known 4-[(2-methyl-3-(furylthio)]pentanone at 0.3 ppm rtc.

Results of the evaluation (the numbers correspond to the flavoring compositions 3 and 4 indicated above, when compared on blind tests to the unflavored and flavored products obtained with compositions 1 and 2, and to each other):

Odor:
3) Meatier, cooked, good coverage of the base taste
4) Less performant, less impact.
Taste:
3) Rounder, mellower, good marriage with the fats in the base, a bit to strong. Better dosed at 0.2 ppm dosage.
4) Weaker, different character, distinctly less mouthfeel, similar to known furanthiols.

C. Cream of Mushroom Soup

Samples of sterilized cream of mushroom soups were prepared by using an appropriate standard mushroom soup base, flavored under the conditions indicated below, and sterilizing for 65 minutes at 121° C.

The products were flavored as follows:
1) without flavor
2) with a mushroom type flavor (Mushroom 589085 spm, origin: Firmenich S A) at 0.2% rtc
3) with a mushroom type flavor (Mushroom 589085 spm, origin: Firmenich S A) at 0.2% rtc plus 3-[(2-methyl-3-furyl)thio]butanal at 0.3 ppm.
4) with a mushroom type flavor (Mushroom 589085 spm, origin: Firmenich S A) at 0.2% rtc plus 3-[(2-methyl-3-furyl)thio]butanal at 0.6 ppm.

Results of the blind evaluation of these products (the numbers correspond to the flavoring compositions 3 and 4 indicated above, when compared on blind tests to the unflavored and flavored products obtained with compositions 1 and 2):
Odor:
3) More savory, very pleasant
4) A bit overdosed.
Taste:
3) Rounder, creamy, savory, excellent mouthfeel
4) Over dosed, very creamy, mouthfeel much too rich covering the rest of the flavor.

D. Potato Chips

Potato chips were treated in a generally known manner with a standard tomato ketchup snack seasoning, and flavored under the conditions indicated below:
1) without flavor
2) with the tomato ketchup seasoning at 6% rtc
3) with the tomato ketchup seasoning at 6% rtc plus 3-[(2-methyl 3-furyl)thio]butanal at 0.15 ppm.

The various samples of chips (the numbers correspond to the flavoring composition 3, when compared on blind tests to the unflavored and flavored chips obtained with compositions 1 and 2) and the results of the evaluations were the following:
Odor:
3) Increased savory sensation, more appetizing
Taste:
3) Acidity has been covered and the savory character enhanced, relative to the tomato ketchup seasoning.

The invention claimed is:
1. A compound of formula

(I)

wherein R represents a group of formula

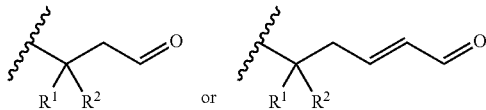

R1 representing a hydrogen atom or a methyl group and R2 representing a $C_1$ to $C_6$ linear or branched, saturated or unsaturated hydrocarbon group.

2. A compound according to claim 1, wherein R represents a group of formula

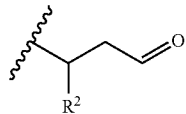

in which R2 is defined as in claim 1.

3. 3-[(2-Methyl-3-furyl)thio]butanal.

4. A flavoring ingredient in the form of a composition comprising:
   i) at least a compound (I) as defined in claim 1;
   ii) at least one ingredient selected from the group consisting of a flavor carrier, flavor base; and
   iii) optionally at least one flavor adjuvant.

5. A flavoring composition as in claim 4, comprising 3-[(2-methyl-3-furyl)thio]butanal.

6. A flavored article comprising:
   i) as flavoring ingredient, at least one compound of formula (I), as defined in claim 1; and
   ii) a foodstuff or oral care product base, or another edible or chewable product base.

7. A flavored article according to claim 6, in the form of a bakery or confectionery product, a chewing gum, a breath freshening film, a ready to cook or ready to eat food, a beverage, a soup, a gravy or a sauce product, a mayonnaise, a pizza, a meat preparation, a cheese preparation, a marinade or coatings for meat or fish, a preparation for injection into meat or fish, a chip, a savory cracker, a vegetable preparation, a soup cube, or an oral care product.

8. A flavored article according to claim 6, in the form of a confectionery product or of a dairy product.

9. A flavored article according to claim 6, wherein the compound (I) is 3-[(2-methyl-3-furyl)thio]butanal.

10. A method to enhance, improve or modify the taste and/or texture of a flavoring composition or a flavoured product, which comprises adding thereto a compound of formula (I) as defined in claim 1.

11. A method to enhance, improve or modify the taste and/or texture of a flavoring composition or a flavoured product, which comprises adding thereto appropriate precursors, a sulfur containing compound, a sugar and an aldehyde, and reacting said precursors under temperature and pH conditions allowing formation of a compound of formula (I) as defined in claim 1.

12. A method according to claim 10, wherein the compound (I) is 3[(2-methyl-3-furyl)thio]butanal.

13. A flavored article according to claim 8, wherein said confectionery product is hard-boiled candy; or wherein said dairy product is milk, cooked milk, caramel, custard, sabaillon or yoghurt.

* * * * *